United States Patent [19]

Motono

[11] Patent Number: 4,981,485
[45] Date of Patent: Jan. 1, 1991

[54] HAIR-DYEING COMPOSITION COMPRISING TANNINS AND WATER SOLUBLE SALTS

[75] Inventor: Masahiro Motono, Kurume, Japan

[73] Assignees: Sansho Seiyaku Co., Ltd., Fukuoka; Teruaki Hayashi, Hyogo, both of Japan

[21] Appl. No.: 323,643

[22] Filed: Mar. 15, 1989

[30] Foreign Application Priority Data

Mar. 30, 1988 [JP] Japan ............................ 63-78371

[51] Int. Cl.$^5$ ................................................ A61K 7/13
[52] U.S. Cl. .......................................... 8/405; 8/406; 8/429; 8/424; 8/423; 560/68
[58] Field of Search ................. 8/405, 406, 429, 424, 8/423; 560/68

[56] References Cited

U.S. PATENT DOCUMENTS 4,517,175  5/1985  Iwabuchi et al. ..................... 424/70
4,530,829  7/1985  Abe .................................. 424/70

FOREIGN PATENT DOCUMENTS 161073    4/1984   European Pat. Off. .
2028818  12/1970   Fed. Rep. of Germany .
53-72836   6/1978   Japan .
60-048916  3/1985   Japan .
62-132813  6/1987   Japan .
63-041414  2/1988   Japan .

*Primary Examiner*—Paul Lieberman
*Assistant Examiner*—James M. Silbermann
*Attorney, Agent, or Firm*—Jordan and Hamburg

[57] ABSTRACT

Disclosed is a hair-dyeing composition comprising one or more tannins and one or more compounds selected from water-soluble zinc, copper, tin, magnesium and aluminum salts. The composition may be in the form of either a one-solution-type or a two-solution-type. The composition may dye hair in any desired color, and the color fastness of the dyed hair is excellent.

18 Claims, No Drawings

HAIR-DYEING COMPOSITION COMPRISING TANNINS AND WATER SOLUBLE SALTS

BACKGROUND OF THE INVENTION

1. Field of the Invention

The present invention relates to a hair-dyeing composition comprising one or more tannins and one or more metal salts. The composition is safe and does not damage the skin or hair. Using the composition, hair can be dyed in various colors.

2. Prior Art

In general, a so-called gray-hair-dyeing composition for dyeing gray hair of the aged is widely used. On the other hand, a so-called "dressing hairdyeing", which dyes hair into colors other than black, such as brown, light brown, yellow or gold, for the decorative purpose of modifying the personal appearance (looks) and matching with make-up and clothing, has become popular these days.

Hitherto, conventional dressing hair-dyeing compositions have comprised a main agent of an aromatic amino compound, such as p-toluenediamine, p-aminophenol, 2-amino-5-hydroxytoluene, 5-amino-2-hydroxytoluene, ophenylenediamine or o-aminophenol and a retouching agent of m-phenylenediamine, pyrogallol or resorcinol. The composition is oxidized and colored in the presence of an oxidizing agent such as hydrogen peroxide so as to color a hair into the desired color of light reddish brown, yellowish gold, reddish yellow or orange.

In the prior art, oxidizing dyes are essentially used in the dressing hair-dyeing compositions for dyeing hair into various colors other than black. However, the oxidizing agents to be used in hair-dyeing with this composition often damage the hair and skin.

SUMMARY OF THE INVENTION

The object of the present invention is to provide a non-oxidizing type hair-dyeing composition which may dye hair in any desired color without damaging the hair and skin.

The present inventor studied the coloration by combination of tannins and metal salts and has found that reaction of tannins and metal salts of zinc, copper, tin, magnesium or aluminum forms various colors of dark or light or dense or sparse brown, yellow or green. The present invention has thus been completed on the basis of such finding.

The present invention provides a hair-dyeing composition comprising one or more tannins and one or more compounds selected from water-soluble zinc, copper, tin, magnesium and aluminum salts; a hair-dyeing composition additionally containing one or more compounds selected from L-cysteine and salts thereof, sodium sulfite, sodium hydrogen sulfite and vitamin E, in addition to the tannin(s) and water-soluble salt(s); a one-solution-type hair-dyeing composition comprising one or more tannins and one or more compounds selected from water-soluble zinc, copper, tin, magnesium and aluminum as a mixture; and a two-solution-type hair-dyeing composition composed of a tannin-containing solution and an aqueous solution of one or more compounds selected from water-soluble zinc, copper, tin, magnesium and aluminum salts.

DESCRIPTION OF THE PREFERRED EMBODIMENTS

In general, tannins are polyoxyphenols existing in plant components and it is said that they have an astringent action to the skin and mucosa. Because of this action, in the past tannins have widely been utilized as a tanning agent, an antidiarrheal and an antiinflammatory agent.

Tannins are roughly grouped into pyrogalloltannins and catechol-tannins, any of which can be used in the present invention. In particular, geraniintannin and tanniic acid in the group of pyrogallol-tannins and catechin-tannin in the group of catechol-tannins are preferably used.

Geraniintannin is especially preferred as it has a high dyability.

Geraniintannin is known as the main component in the herb cranesbill (*Geramium nepalense var. thunbergii*). It does not taste bitter and hardly stimulates the skin and mucosa, although it has a strong binding capacity with proteins.

Geraniintannin is derived from cranesbill, an herb. A powdered form of the herb is extracted with a mixed solvent of ether/water (3/1), and the ether layer is harvested. This is concentrated under reduced pressure and ethanol is added thereto. The resulting mixture is discolored, filtered and further concentrated under reduced pressure. The concentrated liquid is dried to obtain a powder. The powder thus obtained contains geraniintannin in an amount of about 90%.

The water-soluble zinc, copper, tin, magnesium and aluminum salts for use in the present invention may be in the form of a water-soluble salt, such as chloride, acetate, sulfate or phosphate, of the respective metal. In particular, stannous chloride, zinc acetate, cupric chloride, magnesium chloride, aluminum chloride and zinc phosphate are preferred.

The hair-dyeing composition of the present invention comprises one or more of the above-mentioned tannins and one or more compositions selected from the above-mentioned water-soluble zinc, copper, tin, magnesium and aluminum salts. The composition may be in any form of one-solution-type and two-solution-type compositions, which may properly be selected in accordance with the use of the composition.

When catechin-tannin or catechol-tannin is used, the tin salt forms a yellowish brown color, the zinc salt a reddish brown color, the copper salt a yellowish green color, the magnesium salt a liver brown color and the aluminum salt a reddish brown color; when geraniintannin or pyrogallol-tannin is used, the zinc salt forms a yellow color, the copper salt a green color, the tin salt a yellow color, the magnesium salt a pale yellow color and the aluminum salt a gold color; and when tannic acid is used, the copper salt forms a green color, and the tin salt and zinc salt form a white color.

On the basis of these color tones, plural tannins may be combined so as to control the density and deepness of the color tone to be formed on the hair dyed with the composition.

When two or more kinds of the water-soluble zinc, copper, tin, magnesium and aluminum salts are combined, intermediate colors may be obtained.

When the hair-dyeing composition of the present invention is a one-solution-type composition, it is in the form of an aqueous solution containing one or more tannins in an amount of from 0.1 to 10.0% by weight, preferably from 1.0 to 5.0% by weight, and one or more water-soluble zinc, copper, tin, magnesium and/or aluminum salts in an amount of from 0.01 to 5.0% by weight, preferably from 1.0 to 3.0% by weight. A polyhydric alcohol such as propylene glycol or glycerin or ethanol is added to the aqueous solution to form a liquid, emulsion or cream, which may directly be applied to hair to dye the same in a desired color. Alternatively, it may be incorporated into a shampoo or rinse.

When the composition of the present invention is a two-solution-type hair-dyeing composition, a polyhydric alcohol such as propylene glycol or glycerin or ethanol is added to an aqueous solution containing one or more tannins in an amount of from 0.1 to 1.0% by weight, preferably from 1.0 to 5.0% by weight, to form a first solution.

On the other hand, ethanol is added to an aqueous solution containing one or more water-soluble zinc, copper, tin, magnesium and/or aluminum salts in an amount of from 0.1 to 10.0% by weight, preferably from 2.0 to 5.0% by weight, to form a second solution.

Addition of one or more components selected from sodium sulfite, sodium hydrogen sulfite, L-cysteine and L-cysteine hydrochloride and resins for hair such as ethoxyethyl acrylate/hydroxyethyl acrylate copolymer or cationated cellulose to the hair dyeing composition of the present invention is advantageous, since the hair as dyed with the resulting composition may have an elevated color fastness even after repeated hair-shampooing.

The amount of the above-noted additives to be added to the composition of the invention is from 0.1 to 5.0% by weight, preferably from 0.5 to 3.0% by weight. They may be added to the mixture of the two components for the one-solution-type composition, or may be added to the tannin-containing aqueous solution for the two-solution-type composition.

When the one-solution-type hair-dyeing composition of the present invention is actually used for hair-dyeing, the mixture comprising both tannin(s) and metal salt(s) may be directly applied to the hair to be dyed.

When the two-solution type hair-dyeing composition of the invention is actually used for hair-dyeing, the first solution is first applied to the hair to be dyed and kept as it is until the solution becomes dried, or the hair is dried with a drier, and the second solution is then applied to the hair.

Next, the following examples illustrate some embodiments of the hair-dyeing composition of the present invention and the hair-dyeing method using the composition, which, however, do not whatsoever restrict the scope of the present invention.

EXAMPLE 1

Two-solution-type Composition 1.0% geraniintannin, 5.0% propylene glycol, 5.0% ethanol (95%), 1.2% carboxyvinyl polymer, 0.5% l-cysteine hydrochloride and 87.3% pure water were blended to form a first solution.

5.0% stannous chloride, 40.0% ethanol and 55.0% pure water were blended to form a second solution. (The "percentage" is all by weight.)

EXAMPLE 2

One-solution-type Composition 1.0% geraniintannin, 5.0% propylene glycol, 30.0% ethanol, 1.0% cupric chloride, 0.5% L-cysteine hydrochloride and 62.5% pure water were blended to form a hair-dyeing composition. (The "percentage" is all by weight.)

EXPERIMENTAL EXAMPLE

Hair-dyeing Test Using Various Tannins and Various Zinc, Copper, Tin, Magnesium and Aluminum Salts (a) Samples:
(1) First Solution:
Pure water was added to a composition consisting of 5.0% ethanol, 5.0% propylene glycol, 0.8% carboxyvinyl polymer and 2.0% catechin-tannin, and the resulting solution was gelled with potassium carbonate.
Second Solution:
Aqueous 5% zinc acetate solution.
(2) First Solution:
Pure water was added to a composition consisting of 5.0% ethanol, 5.0% propylene glycol, 0.8% carboxyvinyl polymer and 2.0% geraniintannin, and the resulting solution was gelled with potassium carbonate.
Second Solution:
Aqueous 5% stannous chloride solution.
(3) First Solution:
Pure water was added to a composition consisting of 5.0% ethanol, 5.0% propylene glycol, 0.8% carboxyvinyl polymer, 1.0% catechin-tannin and 1.0% geraniintannin, and the resulting solution was gelled with potassium carbonate.
(4) First Solution:
Pure water was added to a composition consisting of 5.0% ethanol, 5.0% propylene glycol, 0.8% carboxyvinyl polymer and 2.0% catechin-tannin, and the resulting solution was gelled with potassium carbonate.
Second Solution:
Aqueous 5% cupric chloride solution.
(5) First Solution:
Pure water was added to a composition consisting of 5.0% ethanol, 5.0% propylene glycol, 0.8% carboxyvinyl polymer and 2.0% geraniintannin, and the resulting solution was gelled with potassium carbonate.
Second Solution:
Aqueous 5% cupric chloride solution.
(6) First Solution:
Pure water was added to a composition consisting of 5.0% ethanol, 5.0% propylene glycol, 0.8% carboxyvinyl polymer and 2.0% catechin-tannin, and the resulting solution was gelled with potassium carbonate.
Second Solution:
Aqueous 5% magnesium chloride solution.
(7) First Solution:
Pure water was added to a composition consisting of 5.0% ethanol, 5.0% propylene glycol, 0.8% carboxyvinyl polymer and 2.0% geraniintannin, and the resulting solution was gelled with potassium carbonate.
Second Solution:
Aqueous 5% magnesium chloride solution.
(8) First Solution:
Pure water was added to a composition consisting of 5.0% ethanol, 5.0% propylene glycol, 0.8% carboxyvinyl polymer and 2.0% catechin-tannin, and the resulting solution was gelled with potassium carbonate.

Second Solution:
Aqueous 5% aluminum chloride solution.
(9) First Solution:
Pure water was added to a composition consisting of 5.0% ethanol, 5.0% propylene glycol, 0.8% carboxyvinyl polymer and 2.0% geraniintannin, and the resulting solution was gelled with potassium carbonate.
Second Solution:
Aqueous 5% aluminum chloride solution.
(The "percentage" is all by weight.)
(b) Test Method:
1 ml of the first solution of each of Samples (1) to (9) was applied to the hair of the back of a ddy mouse (male, 7 to 10-week age). After left as it was for about 5 minutes, the hair was dried with hot air from a drier, and about 1 ml of the corresponding second solution was applied to the hair. The hue of the dye formed and the color of the hair dyed with the dye were observed.
(c) Test Result:
The test result are shown in the Table below.

| Sample No. | Hue of Dye | Color of Dyed Hair |
| --- | --- | --- |
| (1) | pale yellowish brown | pale yellow |
| (2) | ocher yellow | yellow |
| (3) | ocher yellow | gold |
| (4) | yellowish green | pale yellowish green |
| (5) | dark green | pale green |
| (6) | liver brown | ultra-pale yellow |
| (7) | yellowish brown | ultra-pale yellow |
| (8) | reddish brown | ultra-pale light brown |
| (9) | ocher yellow | pale yellow |

The hair-dyeing composition of the present invention is safe, without damaging the skin or hair, and it can easily be used for dyeing a hair into various colors. The composition is therefore an extremely useful dressing hair-dyeing composition.

While the invention has been described in detail and with reference to specific embodiments thereof, it will be apparent to one skilled in the art that various changes and modifications can be made therein without departing from the spirit and scope thereof.

What is claimed is:

1. A hair-dyeing composition comprising an aqueous solution of at least one tannin and at least one compound selected from the group consisting of water-soluble zinc, copper, tin, magnesium and aluminum salts said tannin being present in an amount ranging from 0.1 to 10% by weight and said water-soluble salt being present in an amount ranging from 0.01 to 5% by weight.

2. A hair-dyeing composition as in claim 1, wherein said tannin is selected from the group consisting of geraniintannin, tannic acid, catechin-tannin and mixtures thereof.

3. A hair-dyeing composition as in claim 1, wherein said water-soluble salt is selected from the group consisting of zinc acetate, cupric chloride, cuprous chloride, magnesium chloride, aluminum chloride and mixtures thereof.

4. A hair-dyeing composition as in claim 1, wherein said tannin is present in an amount ranging from 1 to 5% by weight and said water-soluble salt is present in an amount ranging from 1 to 3% by weight.

5. A hair-dyeing composition as in claim 1, wherein said aqueous solution further comprises at least one additive selected from the group consisting of L-cysteine, salts of L-cysteine and resins for hair.

6. A hair-dyeing composition as in claim 5, wherein said resins for hair are selected from the group consisting of ethoxyethyl acrylate/hydroxyethyl acrylate copolymer, cationated cellulose and mixtures thereof.

7. A hair-dyeing composition as in claim 5, wherein said additive is present in an amount ranging from 0.1 to 5.0% by weight.

8. A hair-dyeing composition as in claim 7, wherein said additive is present in an amount ranging from 0.5 to 3.0% by weight.

9. A hair-dyeing composition comprising a first aqueous solution of at least one tannin, and a second aqueous solution of at least one compound selected from the group consisting of water-soluble zinc, copper, tin, magnesium and aluminum salts said tannin being present in an amount ranging from 0.1 to 10% by weight and said water-soluble salt being present in an amount ranging from 0.01 to 5% by weight.

10. A hair-dyeing composition as in claim 9, wherein said tannin is selected from the group consisting of geraniintannin, tannic acid, catechin-tannin and mixtures thereof.

11. A hair-dyeing composition as in claim 9, wherein said water-soluble salt is selected from the group consisting of zinc acetate, cupric chloride, cuprous chloride, magnesium chloride, aluminum chloride and mixtures thereof.

12. A hair-dyeing composition as in claim 9, wherein said tannin is present in an amount ranging from 1 to 5% by weight and said water-soluble salt is present in an amount ranging from 1 to 3% by weight.

13. A hair-dyeing composition as in claim 9, wherein said first solution further comprises a polyhydric alcohol in an amount ranging from 0.1 to 10% by weight.

14. A hair-dyeing composition as in claim 9, wherein said second solution further comprises ethanol in an amount ranging from 0.1 to 10% by weight.

15. A hair-dyeing composition as in claim 9, wherein said first solution further comprises at least one additive selected from the group consisting of L-cysteine, salts of L-cysteine and resins for hair.

16. A hair-dyeing composition as in claim 15, wherein said resins for hair are selected from the group consisting of ethoxyethyl acrylate/hydroxyethyl acrylate copolymer, cationated cellulose and mixtures thereof.

17. A hair-dyeing composition as in claim 15, wherein said additive is present in an amount ranging from 0.1 to 5.0% by weight.

18. A hair-dyeing composition as in claim 15, wherein said additive is present in an amount ranging from 0.5 to 3.0% by weight.

* * * * *